(12) United States Patent
Shinji

(10) Patent No.: US 11,805,988 B2
(45) Date of Patent: Nov. 7, 2023

(54) ENDOSCOPE SYSTEM

(71) Applicant: OLYMPUS CORPORATION, Tokyo (JP)

(72) Inventor: Sho Shinji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 483 days.

(21) Appl. No.: 17/108,216

(22) Filed: Dec. 1, 2020

(65) Prior Publication Data

US 2021/0106215 A1 Apr. 15, 2021

Related U.S. Application Data

(63) Continuation of application No. PCT/JP2018/021597, filed on Jun. 5, 2018.

(51) Int. Cl.
*A61B 1/00* (2006.01)
*A61B 1/045* (2006.01)
*A61B 1/06* (2006.01)

(52) U.S. Cl.
CPC .......... *A61B 1/045* (2013.01); *A61B 1/00006* (2013.01); *A61B 1/000094* (2022.02);
(Continued)

(58) Field of Classification Search
CPC . A61B 1/045; A61B 1/000094; A61B 1/0605; A61B 1/00006; A61B 1/06;
(Continued)

(56) References Cited

U.S. PATENT DOCUMENTS

| 3,570,625 | A | 3/1971 | Allen et al. |
|---|---|---|---|
| 6,464,633 | B1 | 10/2002 | Hosoda et al. |

(Continued)

FOREIGN PATENT DOCUMENTS

| EP | 2229870 A1 | 9/2010 |
|---|---|---|
| EP | 2520214 A1 | 11/2012 |

(Continued)

OTHER PUBLICATIONS

U.S. Office Action dated Oct. 4, 2021 in U.S. Appl. No. 16/702,839.
(Continued)

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An endoscope system includes: an illumination portion including an emitter and being configured to radiate illumination light beam onto an imaging subject, the beam having intensity distribution in which light and dark portions are spatially repeated; a controller configured to cause widths of the dark portions to change; an imager configured to acquire a plurality of illumination images of the subject being illuminated with beams in which the widths of the dark portions are different from each other; and at least one processor including hardware, the processor being configured to: create first and second images from each of the illumination images, the first images containing a greater quantity of information about a deep layer of the subject than the second images do; and calculate information about depths of a feature portion in the subject on the basis of changes among the first images and changes among the second images.

9 Claims, 14 Drawing Sheets

(52) U.S. Cl.
CPC .............. *A61B 1/06* (2013.01); *A61B 1/0605* (2022.02); *A61B 1/0638* (2013.01)

(58) Field of Classification Search
CPC . A61B 1/0638; A61B 1/0005; A61B 1/00009; G01B 11/2513
USPC ......................................................... 600/180
See application file for complete search history.

(56) References Cited

U.S. PATENT DOCUMENTS

| | | | |
|---|---|---|---|
| 7,519,096 | B2 | 4/2009 | Bouma et al. |
| 10,251,530 | B2 | 4/2019 | Henley et al. |
| 10,342,459 | B2 | 7/2019 | Yokota |
| 10,972,675 | B2 | 4/2021 | Shinji et al. |
| 11,045,081 | B2 | 6/2021 | Matsumoto et al. |
| 11,070,739 | B2 | 7/2021 | Matsumoto et al. |
| 2002/0165456 | A1 | 11/2002 | Canpolat et al. |
| 2008/0192128 | A1 | 8/2008 | Kempe et al. |
| 2008/0252945 | A1 | 10/2008 | Kempe et al. |
| 2009/0058999 | A1 | 3/2009 | Gono et al. |
| 2010/0048995 | A1 | 2/2010 | Suijver et al. |
| 2010/0195078 | A1 | 8/2010 | Horiuchi et al. |
| 2010/0224796 | A1 | 9/2010 | Mertz et al. |
| 2010/0240953 | A1 | 9/2010 | Murakami |
| 2010/0245551 | A1 | 9/2010 | Morita |
| 2011/0263955 | A1 | 10/2011 | Narita et al. |
| 2012/0123205 | A1 | 5/2012 | Nie et al. |
| 2012/0302847 | A1 | 11/2012 | Ozawa et al. |
| 2012/0327205 | A1 | 12/2012 | Takahashi |
| 2013/0270421 | A1 | 10/2013 | Kanamori et al. |
| 2014/0052005 | A1 | 2/2014 | Yokota |
| 2014/0092227 | A1 | 4/2014 | Kanamori et al. |
| 2014/0267657 | A1 | 9/2014 | Takei et al. |
| 2014/0288365 | A1 | 9/2014 | Henley et al. |
| 2014/0316283 | A1 | 10/2014 | Kaku et al. |
| 2015/0022647 | A1 | 1/2015 | Takei et al. |
| 2015/0238089 | A1 | 8/2015 | Fujinuma et al. |
| 2015/0320296 | A1 | 11/2015 | Morita |
| 2016/0041334 | A1 | 2/2016 | Suijver et al. |
| 2016/0278678 | A1 | 9/2016 | Valdes et al. |
| 2016/0334340 | A1 | 11/2016 | Ollivier et al. |
| 2017/0006202 | A1 | 1/2017 | Otani et al. |
| 2017/0098301 | A1 | 4/2017 | Ikemoto et al. |
| 2017/0143237 | A1 | 5/2017 | Yokota |
| 2017/0231480 | A1 | 8/2017 | Yamazaki |
| 2018/0164221 | A1 | 6/2018 | Singh et al. |
| 2019/0133416 | A1 | 5/2019 | Henley et al. |
| 2019/0274591 | A1 | 9/2019 | Yokota |
| 2020/0099844 | A1 | 3/2020 | Shinji et al. |
| 2020/0099845 | A1 | 3/2020 | Matsumoto et al. |
| 2020/0100650 | A1 | 4/2020 | Oka |
| 2020/0100660 | A1 | 4/2020 | Matsumoto et al. |

FOREIGN PATENT DOCUMENTS

| | | | |
|---|---|---|---|
| EP | 2526854 | A1 | 11/2012 |
| EP | 2979607 | A1 | 2/2016 |
| EP | 3075301 | A1 | 10/2016 |
| EP | 3202306 | A1 | 8/2017 |
| JP | 2009-536066 | A | 10/2009 |
| JP | 2010-213992 | A | 9/2010 |
| JP | 2010-227256 | A | 10/2010 |
| JP | 2012-239816 | A | 12/2012 |
| JP | 2014-18439 | A | 2/2014 |
| JP | 2014-188222 | A | 10/2014 |
| JP | 2015-077415 | A | 4/2015 |
| JP | 2015-231498 | A | 12/2015 |
| JP | 2016-49370 | A | 4/2016 |
| JP | 2016-174836 | A | 10/2016 |
| JP | 2016-198304 | A | 12/2016 |
| JP | 2016-200418 | A | 12/2016 |
| JP | 2016-209466 | A | 12/2016 |
| JP | 2017-042629 | A | 3/2017 |
| WO | 2007/030741 | A2 | 3/2007 |
| WO | 2007/132378 | A2 | 11/2007 |
| WO | 2011/080996 | A1 | 7/2011 |
| WO | 2011/081141 | A1 | 7/2011 |
| WO | 2014/144986 | A1 | 9/2014 |
| WO | 2015/016013 | A1 | 2/2015 |
| WO | 2016/151903 | A1 | 9/2016 |
| WO | 2016/181720 | A1 | 11/2016 |
| WO | 2018/229831 | A1 | 12/2018 |
| WO | 2018/229832 | A1 | 12/2018 |
| WO | 2018/229833 | A1 | 12/2018 |
| WO | 2018/229834 | A1 | 12/2018 |
| WO | 2019/234829 | A1 | 12/2019 |

OTHER PUBLICATIONS

Nayar et al. "Fast Separation of Direct and Global Components of a Scene using High Frequency Illumination." Cited in the ISR for PCT/JP2018/021590 dated Jul. 24, 2018; PCT/JP2018/021597 dated Jul. 24, 2018; PCT/JP2017/021664 dated Aug. 15, 2017; PCT/JP2017/021661 dated Aug. 22, 2017; PCT/JP2017/021665 dated Aug. 22, 2017; and PCT/JP2017/021667 dated Aug. 22, 2017. Published Jul. 2006. pp. 935-944. vol. 25, Issue 3.

Takatani et al. "Decomposition of Reflected and Scattered Lights by Multiple Weighted Measurements." 14th Symposium on Image Recognition and Understanding. Jul. 2011. 14 pages.

Tanaka et al. "Adaptive Frequency Selection under Parallel High-frequency Illumination." 16th Symposium on Image Recognition and Understanding (MIRU2013), Collection of Extended Abstract, Information Processing Society of Japan, Yoshiki Shimotsuma, SS2-33. Cited in the ISR for PCT/JP2017/021661 dated Aug. 22, 2017 and PCT/JP2017/021665 dated Aug. 22, 2017. Jul. 22, 2013. 7 pages.

Takatani et al. "Decomposition of Reflected and Scattered Lights by Multiple Weighted Measurements." , IPSJ SIG Technical Report (CD-ROM), Rombunno. CVIM-177, No. 12, ISSN 2186-2583. vol. 2011, No. 1. Cited in the ISR for PCT/JP2017/021661 dated Aug. 22, 2017 and PCT/JP2017/021665 dated Aug. 22, 2017. Jun. 15, 2011. 13 pages.

U.S. Appl. No. 17/108,205, filed Dec. 1, 2020.

International Search Report dated Aug. 22, 2017, issued in PCT/JP2017/021661, 26 pages.

International Search Report dated Aug. 15, 2017, issued in PCT/JP2017/021664, 14 pages.

International Search Report dated Aug. 22, 2017, issued in PCT/JP2017/021665, 16 pages.

International Search Report dated Aug. 22, 2017, issued in PCT/JP2017/021667, 14 pages.

International Search Report dated Jul. 24, 2018, issued in PCT/JP2018/021590, 23 pages.

International Search Report dated Jul. 24, 2018, issued in PCT/JP2018/021597, 11 pages.

Office Action dated Jun. 19, 2020 received in U.S. Appl. No. 16/691,865, 16 pages.

Office Action dated Dec. 11, 2020 received in U.S. Appl. No. 16/691,961, 11 pages.

Office Action dated Dec. 3, 2020 received in U.S. Appl. No. 16/702,964, 13 pages.

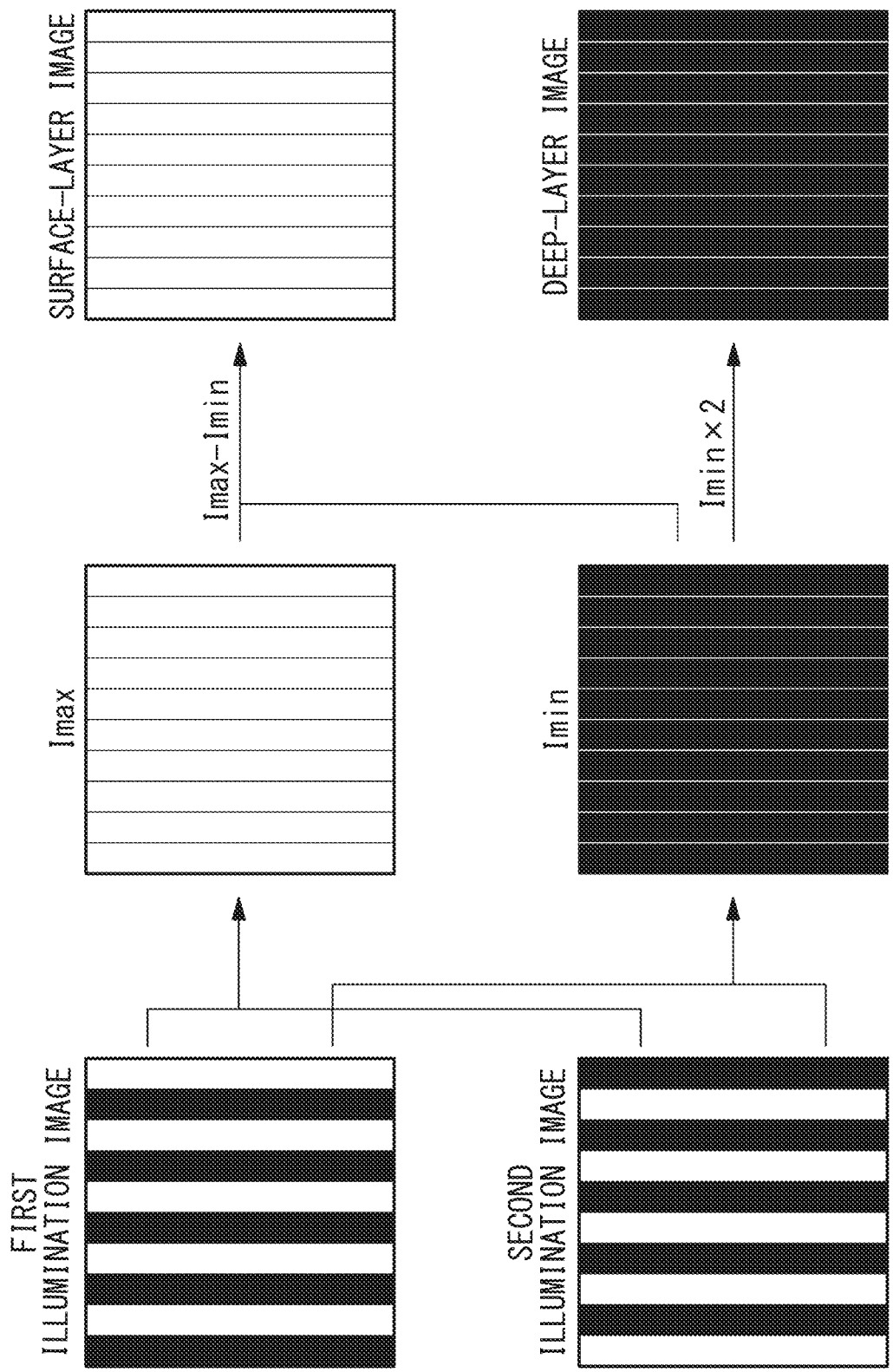

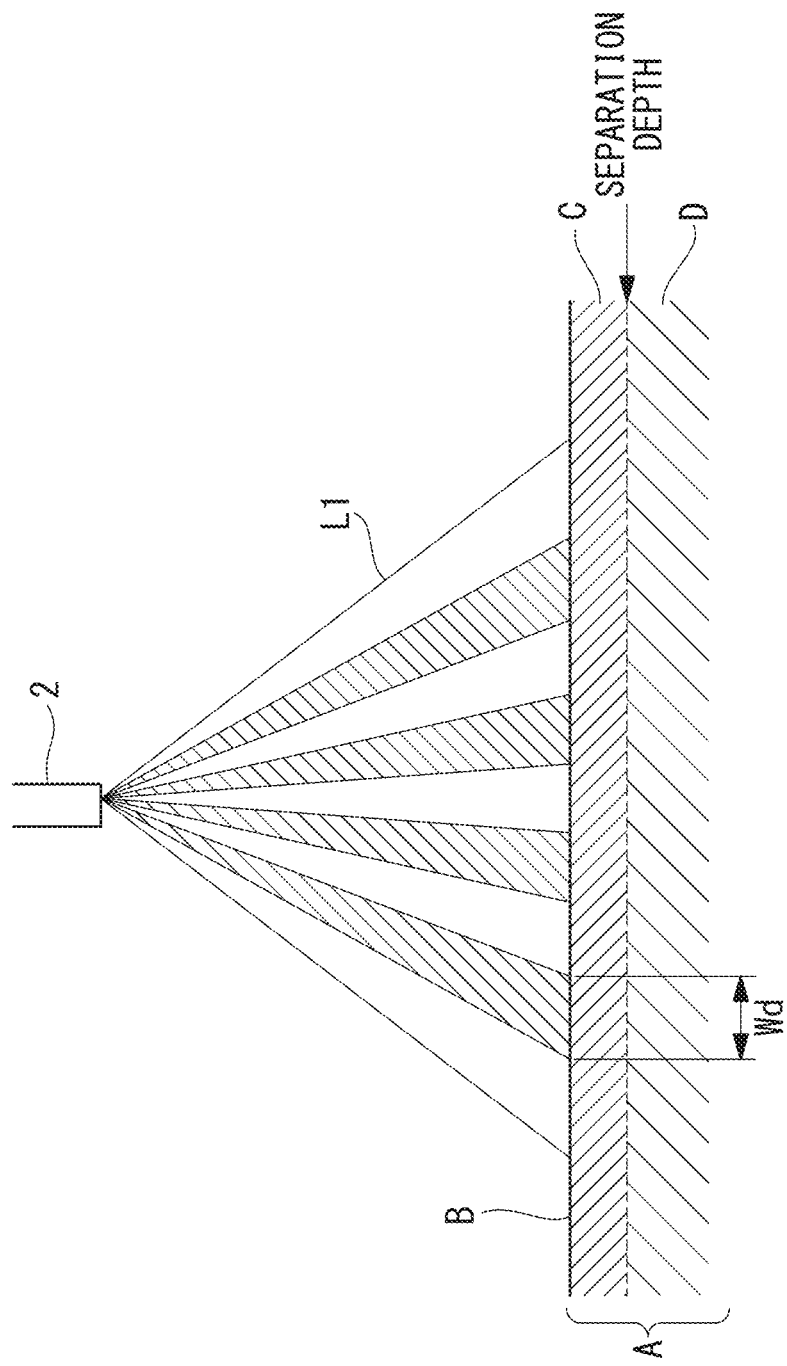

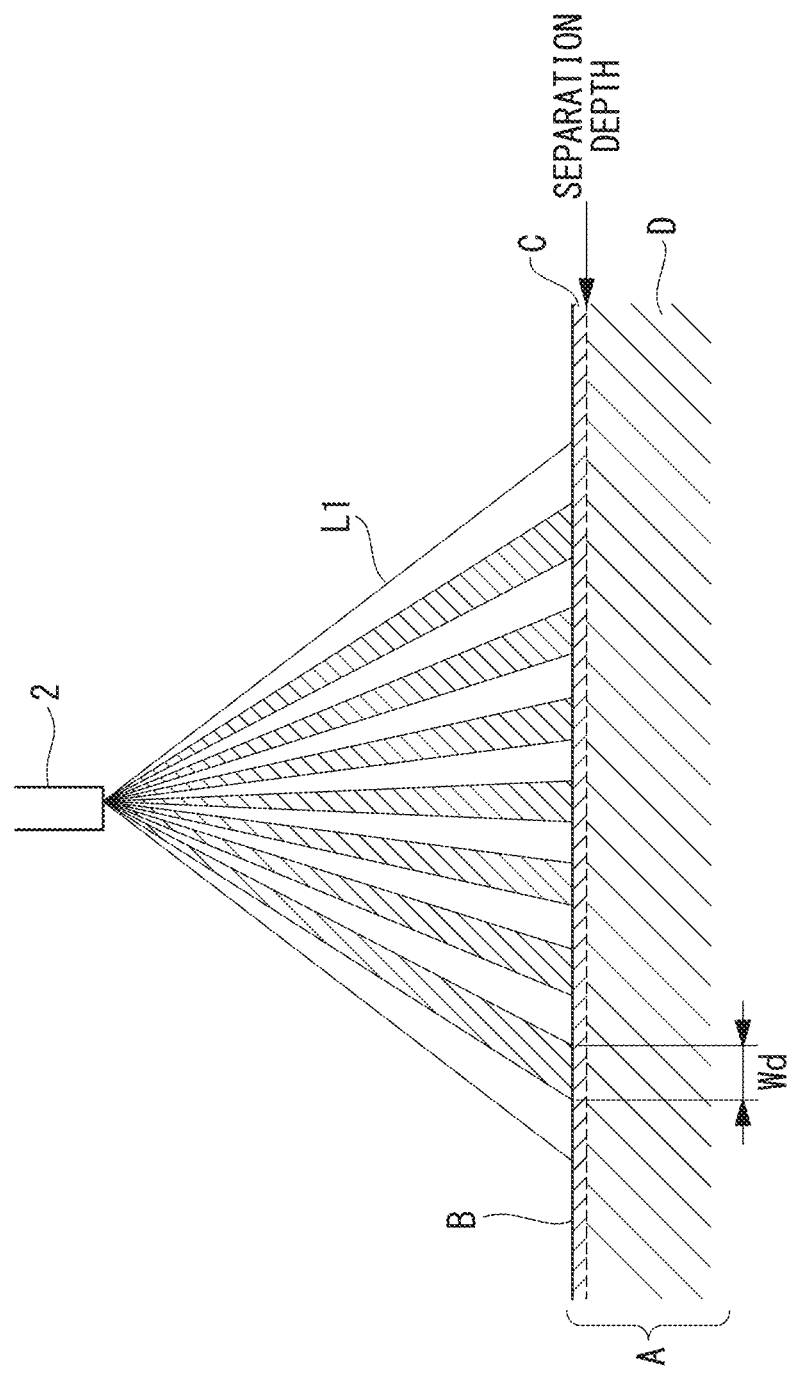

ENDOSCOPE SYSTEM

CROSS-REFERENCE TO RELATED APPLICATIONS

This is a continuation of International Application PCT/JP2018/021597 which is hereby incorporated by reference herein in its entirety.

TECHNICAL FIELD

The present invention relates to an endoscope system.

BACKGROUND ART

In the related art, there is a proposed endoscope system that calculates the thicknesses and the depths of blood vessels in an observation area by utilizing a ratio of imaging signals for three wavelength bands that differ in terms of hemoglobin absorption characteristics (for example, see Patent Literature 1).

CITATION LIST

Patent Literature

{PTL 1} Japanese Unexamined Patent Application, Publication No. 2016-174836

SUMMARY OF INVENTION

An aspect of the present invention is an endoscope system including: an illumination portion that includes an emitter and that is configured to radiate illumination light beam onto an imaging subject, the illumination light beam having intensity distribution in which light portions and dark portions are spatially repeated in a beam cross section perpendicular to an optical axis; a controller configured to cause widths of the dark portions in the intensity distribution of the illumination light beam to change; an imager configured to acquire a plurality of illumination images of the imaging subject being illuminated with illumination light beams in which the widths of the dark portions are different from each other; and at least one processor including hardware, the processor being configured to: create first separation images and second separation images from each of the plurality of illumination images, the first separation images containing a greater quantity of information about a deep layer of the imaging subject than the second separation images do; and calculate information about depths of a feature portion in the imaging subject on the basis of the plurality of the first separation images and the plurality of the second separation images created from the plurality of illumination images, wherein the processor is configured to: create the first and second separation images on the basis of at least two types of intensity values among the intensity values of pixels that are in the illumination images and that respectively correspond to, in the intensity distribution, the light portions, the dark portions, and portions having intensity values that are between those of the light portions and those of the dark portions; and calculate the information about the depths of the feature portion on the basis of changes among the plurality of first separation images and changes among the plurality of second separation images.

BRIEF DESCRIPTION OF DRAWINGS

FIG. 3 is a diagram for explaining a method for creating a surface-layer image and a deep-layer image by means of a separation processing portion.

FIG. 4A is a diagram for explaining the relationship between the widths of dark portions and a separation depth of the illumination light beam.

FIG. 4B is a diagram for explaining the relationship between the widths of the dark portions and the separation depth of the illumination light beam.

DESCRIPTION OF EMBODIMENT

An endoscope system 1 according to an embodiment of the present invention will be described below with reference to the drawings.

Figure 1:
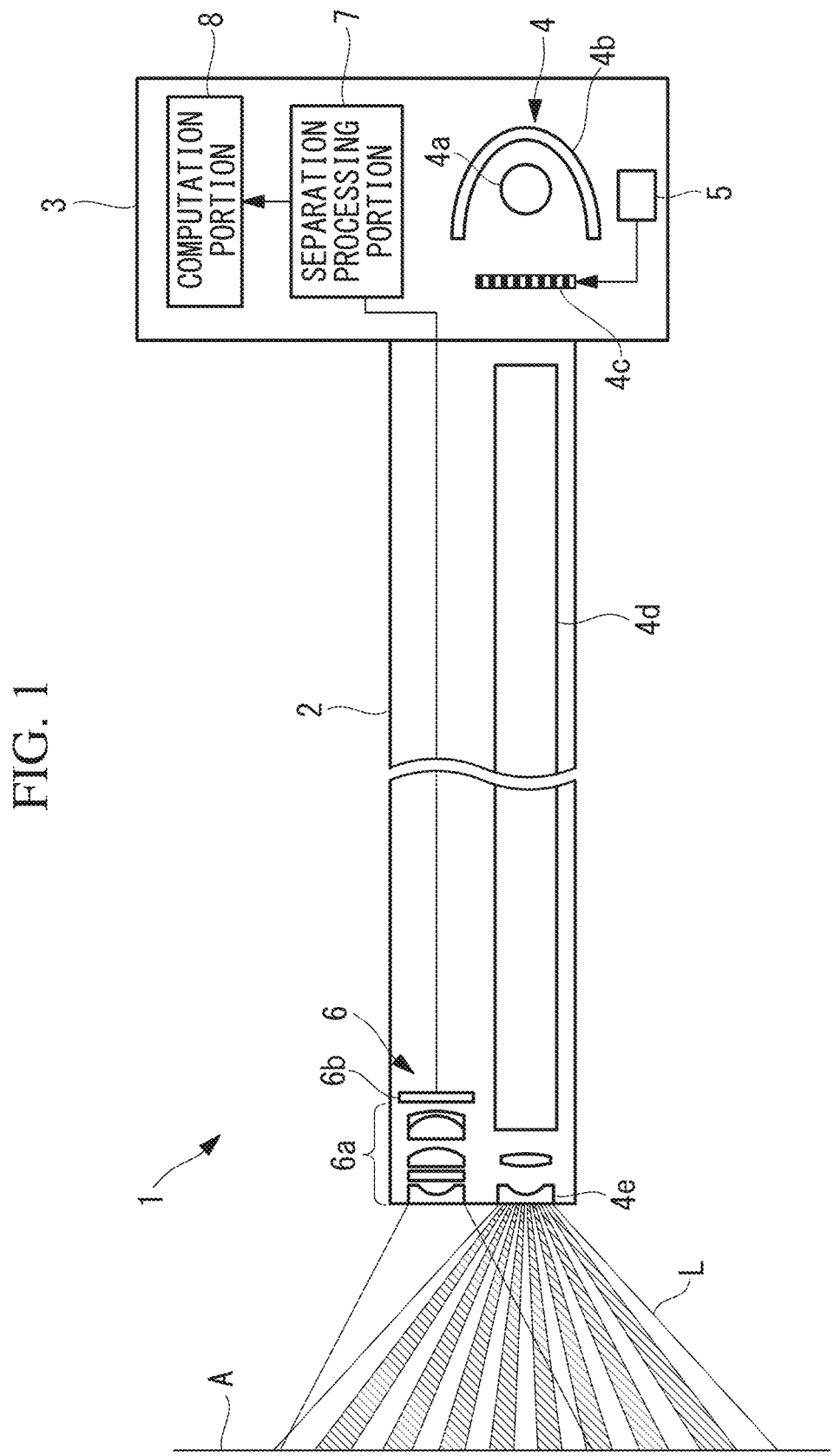
FIG. 1 is an overall configuration diagram of an endoscope system according to an embodiment of the present invention.

As shown in FIG. 1, the endoscope system 1 according to this embodiment includes an endoscope 2 with which the interior of a body is observed and a main body portion 3 that is connected to a proximal end of the endoscope 2.

In addition, the endoscope system 1 includes: an illumination portion 4 that illuminates biological tissue (imaging subject) A in a body with an illumination light beam L having a light-dark pattern; an intensity-distribution changing portion 5 that causes the light-dark pattern of the illumination light beam L to change; an image acquisition portion 6 that acquires an illumination image of the biological tissue A being illuminated with the illumination light beam L; a separation processing portion 7 that creates, from the illumination image, a surface-layer image (second separation image) and a deep-layer image (first separation image); and a computation portion 8 that calculates depth information of a feature portion E (see FIG. 5A) in the biological tissue A on the basis of the surface-layer image and the deep-layer image. The feature portion E is tissue present in the biological tissue A, for example, a blood vessel or a lesion.

Figure 2:
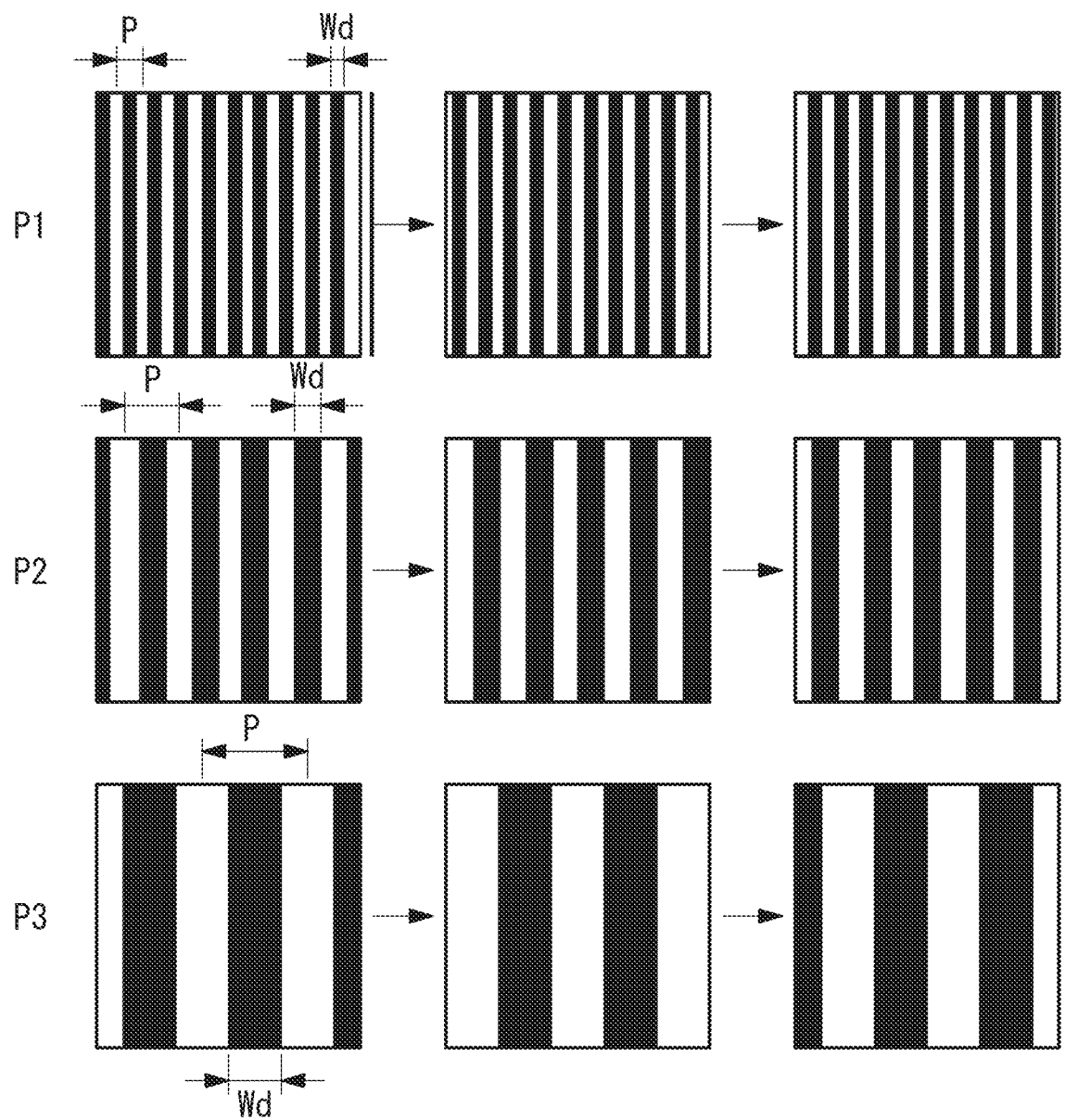
FIG. 2 is a diagram showing an example of the change over time in a light-dark pattern of an illumination light beam.

The illumination portion 4 generates the illumination light beam L, which has a spatially nonuniform intensity distribution in a beam cross section perpendicular to the optical axis, and emits the illumination light beam L toward the biological tissue A from a distal end of the endoscope 2. The illumination light beam L is, for example, single-wavelength light such as white light or infrared light, monochromatic light such as red light, green light, and blue light, or mixed light of a plurality of light beams having different wavelengths. In general, the illumination light beam L has an intensity gradient in which the brightness thereof gradually decreases toward the periphery from the center of the beam. Apart from such an overall intensity gradient of the beam cross section, the illumination light beam L has a light-dark pattern in which light portions having high intensities and dark portions having lower intensities than the light portions are repeated in an alternating manner in the beam cross section. As shown in FIG. 2, the light-dark pattern is a stripe pattern in which straight band-like light portions and dark portions are repeated in an alternating manner only in a width direction orthogonal to longitudinal directions of the light portions and the dark portions. In FIG. 2, open regions represent the light portions and filled regions represent dark portions. In the light-dark pattern in FIG. 2, the width of each of the light portions is the same as the width of each of the dark portions; however, the width of each of the light portions may be different from the width of each of the dark portions.

As shown in FIG. 1, the illumination portion 4 includes a light emitting portion 4a, a reflector 4b, and a mask 4c that are provided in the main body portion 3. In addition, the illumination portion 4 includes an image guide fiber 4d and a projection lens 4e that are provided in the endoscope 2. Light output from the light emitting portion 4a is focused by the reflector 4b and illuminates the mask 4c. The mask 4c has light transmitting regions that allow the light to pass therethrough and light blocking regions that block the light, and thus, a projection pattern corresponding to the light-dark pattern is formed from the light transmitting regions and the light blocking regions. The illumination light beam L having the light-dark pattern is generated as a result of the light passing through the mask 4c. The mask 4c is a liquid crystal element that is capable of electrically controlling light transmittances at respective positions in an entry region at which the light enters. The illumination light beam L generated by the mask 4c is guided by the image guide fiber 4d while preserving the light-dark pattern and is emitted from the distal end of the endoscope 2 by means of the projection lens 4e.

As shown in FIG. 2, the intensity-distribution changing portion 5 causes positions of the light portions and the dark portions in the light-dark pattern and pitches (periods of the light portions and the dark portions) P of the light-dark pattern to change over time. Widths Wd of the dark portions change due to changes in the pitches P (P1, P2, and P3).

Specifically, the intensity-distribution changing portion 5 causes the light-dark pattern to change over time in the width directions of the light portions and the dark portions, and thus, the positions of the light portions and the dark portions are switched with each other. In FIG. 2, the lateral direction represents the flow of time. Accordingly, the light portions and the dark portions are projected at the respective positions in an area irradiated with the illumination light beam L on a surface B of the biological tissue A. The intensity-distribution changing portion 5 causes the positions of the light portions and the dark portions to change over time, subsequently changes the pitches P, and causes the positions of the light portions and the dark portions to change over time again. The intensity-distribution changing portion 5 repeats changing of the pitches P and changing of the positions of the light portions and the dark portions.

The intensity-distribution changing portion 5 includes a control element that controls the light transmittances at the respective positions in the entry region of the mask 4c. The mask 4c consisting of a liquid crystal element is capable of forming an arbitrary projection pattern and is capable of causing the arbitrary projection pattern to change over time. The intensity-distribution changing portion 5 causes the pitches P and the widths Wd of the illumination light beam L to change over time by controlling the light transmittances at the respective positions of the mask 4c in accordance with a program that is set in advance.

The image acquisition portion 6 includes: an image acquisition lens 6a that is provided at the distal end of the endoscope 2 and that collects the light coming from the biological tissue A; and an image acquisition element 6b that captures images of the biological tissue A formed by the image acquisition lens 6a. The illumination images acquired by the image acquisition element 6b are transmitted to the separation processing portion 7 from the image acquisition element 6b.

Here, the intensity distribution of the illumination light beam L radiated onto the biological tissue A is changed over time by means of the intensity-distribution changing portion 5, as shown in FIG. 2. The image acquisition element 6b acquires multiple sets of first illumination images and second illumination images in which the pitches of the light-dark pattern are different from each other. The first illumination images and the second illumination images are images of the biological tissue A illuminated with the illumination light beam L in which the dark portions and the light portions are switched with each other. Therefore, as shown in FIG. 3, the first illumination images and the second illumination images are images in which the projection regions of the light portions and the projection regions of the dark portions are inverted with respect to each other and in which the projection regions of the light portions are complementary with respect to each other and the projection regions of the dark portions are complementary with respect to each other. In the first illumination image and the second illumination image in FIG. 3, open regions represent the projection regions of the light portions and filled regions represent the projection regions of the dark portions.

Therefore, the operation of the intensity-distribution changing portion 5 and that of the image acquisition element 6b are controlled by a controller (not shown) provided in the main body portion 3 so that the timing at which the intensity-distribution changing portion 5 changes the intensity distribution and the timing at which the image acquisition element 6b captures images are synchronized with each other.

As shown in FIG. 3, the separation processing portion 7 creates one set of a surface-layer image and a deep-layer image from each set of the first illumination images and the second illumination images. Regarding pixels at the respective positions of the first and second illumination images, intensity values Imax when the light portions are projected and intensity values Imin when the dark portions are projected are acquired. The separation processing portion 7 calculates intensity values Is of the respective pixels of the surface-layer image from Expression (1) below and creates a surface-layer image having the intensity values Is. In addition, the separation processing portion 7 calculates intensity values Id of the respective pixels of the deep-layer image from Expression (2) below and creates a deep-layer image having the intensity values Id.

$$Is = Imax - Imin \quad (1)$$

$$Id = Imin \times 2 \quad (2)$$

When the illumination light beam L having the light-dark pattern is radiated onto the biological tissue A, which is a scatterer, specular reflected light beams (specular light beams), surface scattered light beams, and interior scattered light beams are generated in the biological tissue A.

The specular light beams are reflected light beams generated by specular reflection of the illumination light beam L at the surface B of the biological tissue A and are generated in the projection regions of the light portions.

The surface scattered light beams are scattered light beams generated as a result of the illumination light beam L entering the biological tissue A from the projection regions of the light portions, passing through a surface layer C while repeatedly scattering, and being emitted from the surface B. Most of the surface scattered light beams are emitted from the projection regions of the light portions.

The interior scattered light beams are scattered light beams generated as a result of the illumination light beam L entering the biological tissue A from the projection regions of the light portions, passing through a deep layer D while repeatedly scattering, and being emitted from the surface B. Some of the interior scattered light beams are emitted from the projection regions of the light portions, and other interior scattered light beams are propagated to the projection regions of the dark portions and are emitted from the projection regions of the dark portions.

In other words, the intensity values Imin of the projection regions of the dark portions in the first and second illumination images are mainly based on the interior scattered light beams and mainly contain information about the deep layer D. Therefore, the deep-layer image based on the intensity values Imin is an image that mainly contains the information about the deep layer D. On the other hand, the intensity values Imax of the projection regions of the light portions in the first and second illumination images are based on the specular light beams, the surface scattered light beams, and the interior scattered light beams and contain information about the surface B, the surface layer C, and the deep layer D. Therefore, the surface-layer image based on the intensity values Is is an image from which the information about the deep layer D is removed and that mainly contains the information about the surface B and the surface layer C.

The separation processing portion 7 creates multiple sets of the deep-layer images and multiple sets of the surface-layer images from the multiple sets of the first illumination images and the second illumination images acquired by the image acquisition portion 6. The created surface-layer images and deep-layer images are transmitted to the computation portion 8.

Here, as shown in FIGS. 4A and 4B, a separation depth between a surface-layer image and a deep-layer image depends on the widths Wd of the dark portions on the surface B of the biological tissue A. The separation depth is an approximate boundary between the depth of the information contained in a surface-layer image and the depth of the information contained in a deep-layer image. In other words, the surface-layer image mainly contains information about layers between the surface B and the separation depth, and the deep-layer image mainly contains information about layers deeper than the separation depth. The position of the separation depth becomes deeper with an increase in the widths Wd of the dark portions.

Figure 5A:
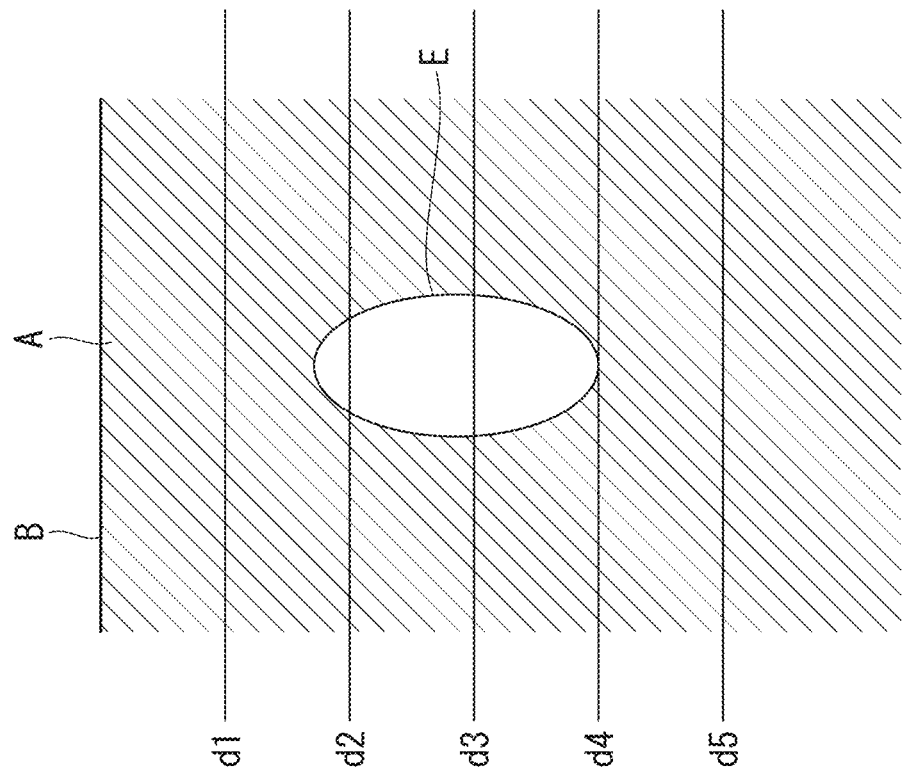
FIG. 5A is a diagram showing the relationship between pitches of the light-dark pattern of the illumination light beams radiated onto the biological tissue and the separation depths thereof.
Figure 5B:
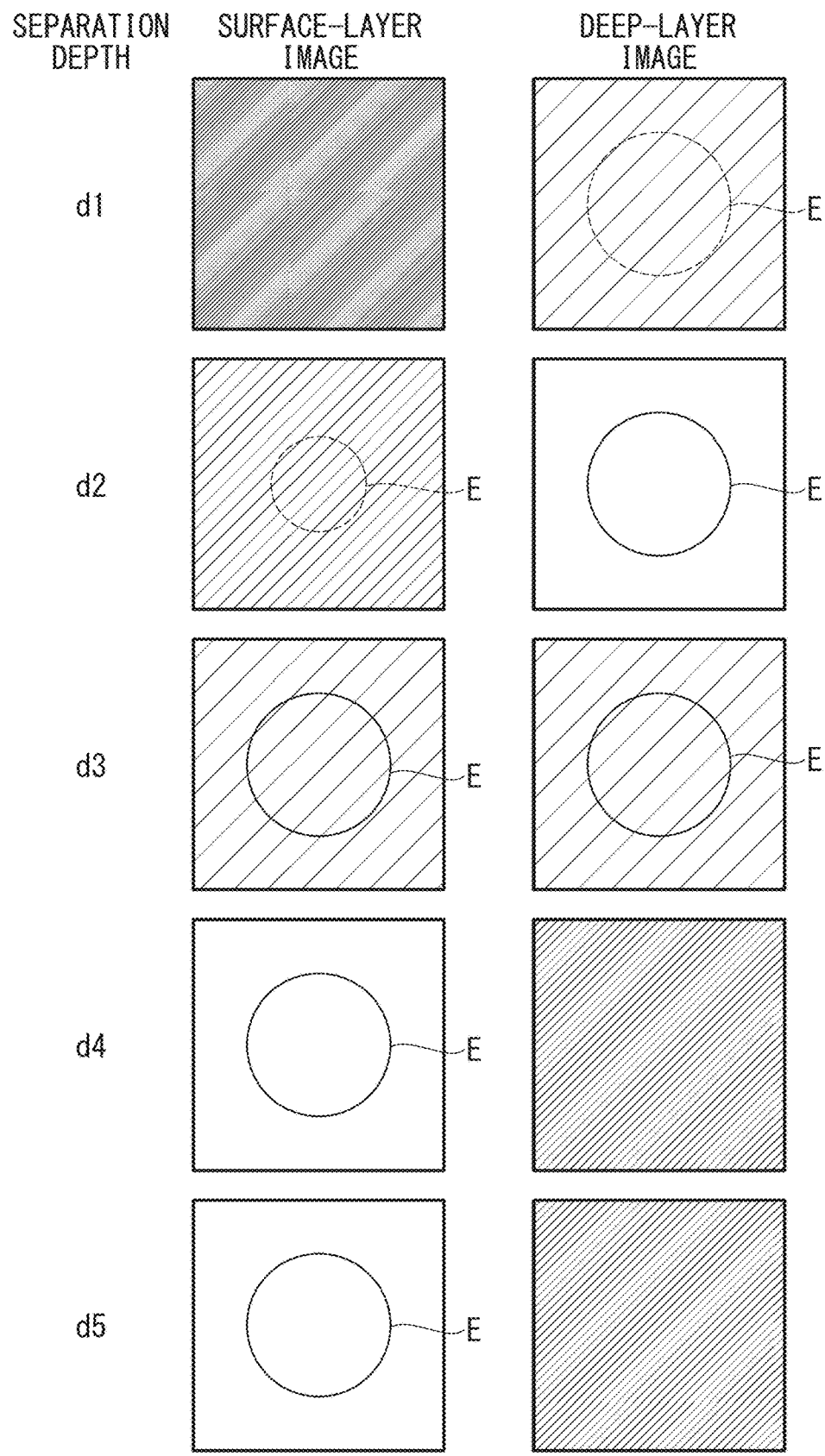
FIG. 5B is a diagram showing surface-layer images and deep-layer images of the biological tissue in FIG. 5A and is a diagram for explaining the relationship between the separation depths and contrasts of the surface-layer images and the deep-layer images.

FIG. 5A shows the relationship between the pitches (P1, P2, P3, P4, and P5) of the light-dark pattern of the illumination light beams L and the separation depths (d1, d2, d3, d4, and d5) of the biological tissue A. FIG. 5B shows examples of the surface-layer images and the deep-layer images based on the illumination light beams L having the respective pitches P1, P2, P3, P4, and P5. As shown in FIG. 5B, the feature portion E at shallower positions than the separation depths is contained in the surface-layer images; however, such a feature portion E is not contained in the deep-layer images. In contrast, the feature portion E at deeper positions than the separation depths is contained in the deep-layer images; however, such a feature portion E is not contained in the surface-layer images.

Figure 6:
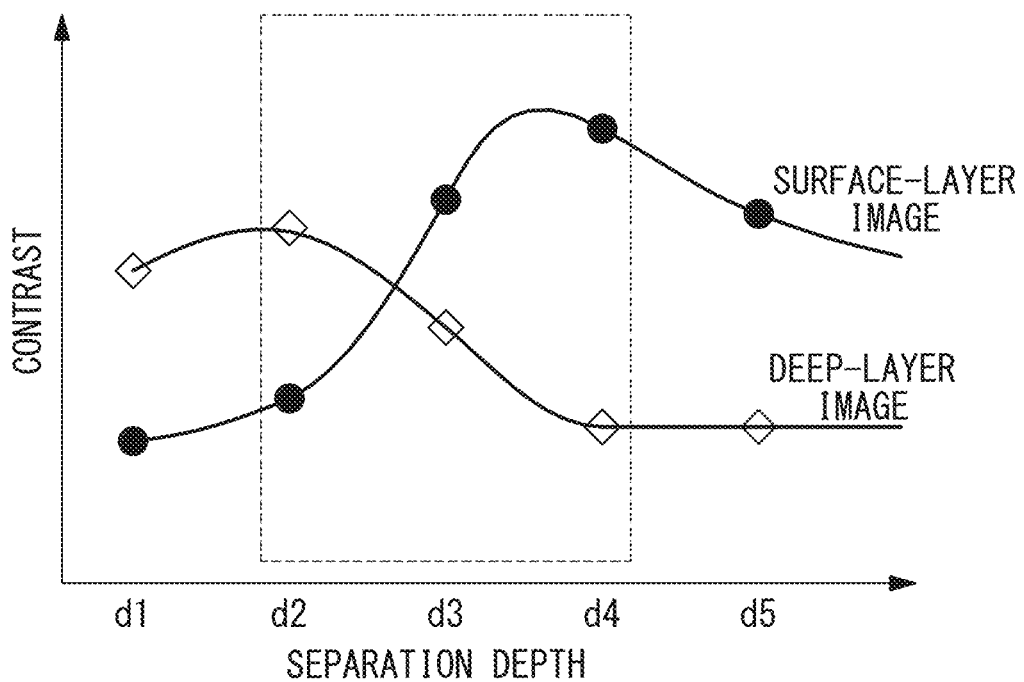
FIG. 6 is a graph showing the relationship between the separation depth and the contrasts of the surface-layer images and the deep-layer images.
Figure 7:
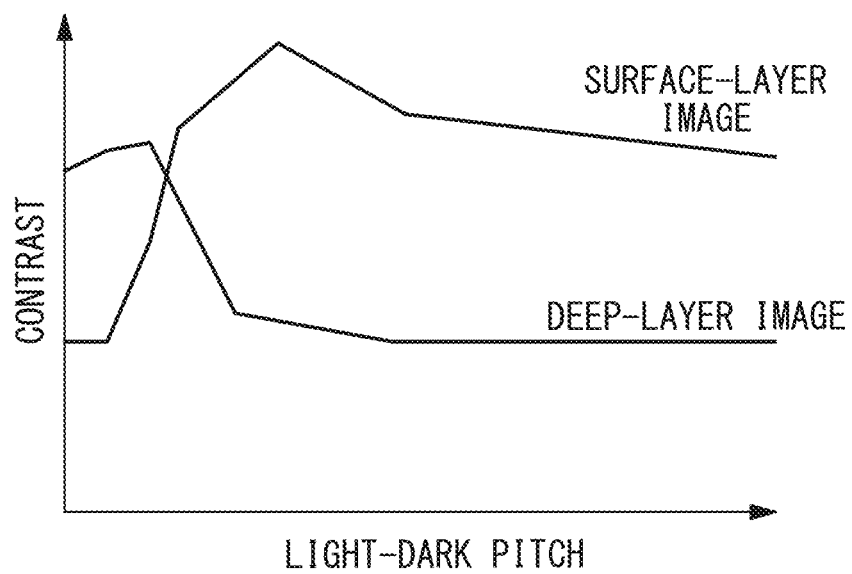
FIG. 7 is a graph showing the relationship between the pitch of the light-dark pattern of the illumination light beam and the contrasts of the surface-layer image and the deep-layer image.
Figure 8:
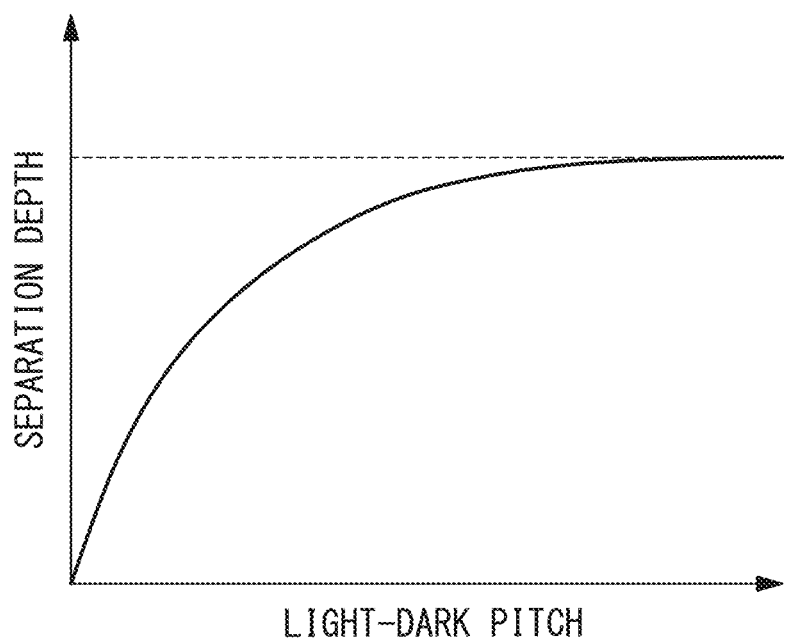
FIG. 8 is a graph showing the relationship between the pitch of the light-dark pattern of the illumination light beam and the separation depth.

The computation portion 8 receives the plurality of deep-layer images and the plurality of surface-layer images from the separation processing portion 7 and calculates the contrast of each of the plurality of deep-layer images and the plurality of surface-layer images. As shown in FIG. 6, the contrasts of the surface-layer images that contain the feature portion E become greater than the contrasts of the surface-layer images that do not contain the feature portion E. Similarly, the contrasts of the deep-layer images that contain the feature portion E become greater than the contrasts of the deep-layer images that do not contain the feature portion E. In FIG. 6, the area surrounded by the broken line is the range of depths at which the feature portion E is present. FIG. 7 shows the relationship between the pitch P of the light-dark pattern and the contrast. FIG. 8 shows the relationship between the pitch P of the light-dark pattern and the separation depth. From FIGS. 7 and 8, the relationship between the separation depth and the contrast in FIG. 6 is obtained.

The computation portion 8 calculates the depths at an end of the feature portion E on a shallow side (surface B side) on the basis of changes in the contrasts of the surface-layer images with respect to the separation depths. For example, the contrast changes considerably between the surface-layer image at the separation depth d1, which does not contain a feature portion E and the surface-layer image at the separation depth d2, which contains a feature portion E. The computation portion 8 indicates, as a result of the calculation, that the depth at the end of the feature portion E on the shallow side is located between d1 and d2 on the basis of said considerable change in the contrast.

In addition, the computation portion 8 calculates depths at an end of the feature portion E on a deep side on the basis of the contrasts of the deep-layer images with respect to the separation depths. The contrast changes considerably between the deep-layer image at the separation depth d3, which contains a feature portion E, and the deep-layer image at the separation depth d4, which does not contain a feature portion E. The computation portion 8 indicates, as a result of the calculation, that the depth at the end of the feature portion E on the deep side is located between d3 and d4 on the basis of said considerable change in the contrast.

The depth information of the feature portion E calculated by the computation portion 8 is, for example, displayed on a display device (not shown) connected to the main body portion 3.

A correspondence table in which the widths Wd of the dark portions and the separation depths are associated with each other may be stored in a storage device (not shown) in the main body portion 3. The computation portion 8 reads out the correspondence table from the storage device and acquires the separation depths of the respective deep-layer images and those of the respective surface-layer images from the correspondence table on the basis of the widths Wd of the dark portions. The information about the widths Wd of the dark portions of the surface-layer images and deep-layer images is, for example, transmitted to the computation portion 8 from the controller.

Next, as shown in FIG. 6, the computation portion 8 creates a graph showing the relationship between the separation depths and the contrasts of the surface-layer images and creates a graph showing the relationship between the separation depths and the contrasts of the deep-layer images. Next, the computation portion 8 detects a separation depth at which the contrast rapidly increases in the graph of the surface-layer images on the basis of the slope of the graph and determines the detected separation depth to be the end of the feature portion E on the shallow side. In addition, the computation portion 8 detects a separation depth at which the contrast rapidly decreases in the graph of the deep-layer images on the basis of the slope of the graph and determines the detected separation depth to be the end of the feature portion E on the deep side.

Although the computation portion 8 may calculate overall contrasts of the surface-layer images and overall contrasts of the deep-layer images, the computation portion 8 may calculate contrasts of portions of the surface-layer images and contrasts of portions of the deep-layer images. In this case, it is preferable that the configuration thereof be such that a surgeon can specify areas in which the contrasts are calculated. For example, the main body portion 3 includes a graphical user interface (GUI). The surgeon can specify desired areas containing the feature portion E by using the GUI.

The separation processing portion 7 and the computation portion 8 are realized in the forms of, for example, programs to be executed by a computer. In other words, a processor such as a central processing unit, a main storage device such as a RAM, and an auxiliary storage device such as a hard disk drive are built into the main body portion 3. The programs for causing the processor to execute the above-described processing performed by the separation processing portion 7 and the computation portion 8 are stored in the auxiliary storage device. The programs are loaded into the main storage device from the auxiliary storage device, and the above-described functions of the separation processing portion 7 and the computation portion 8 are realized as a result of the processor executing the processes in accordance with the programs.

Figure 9:
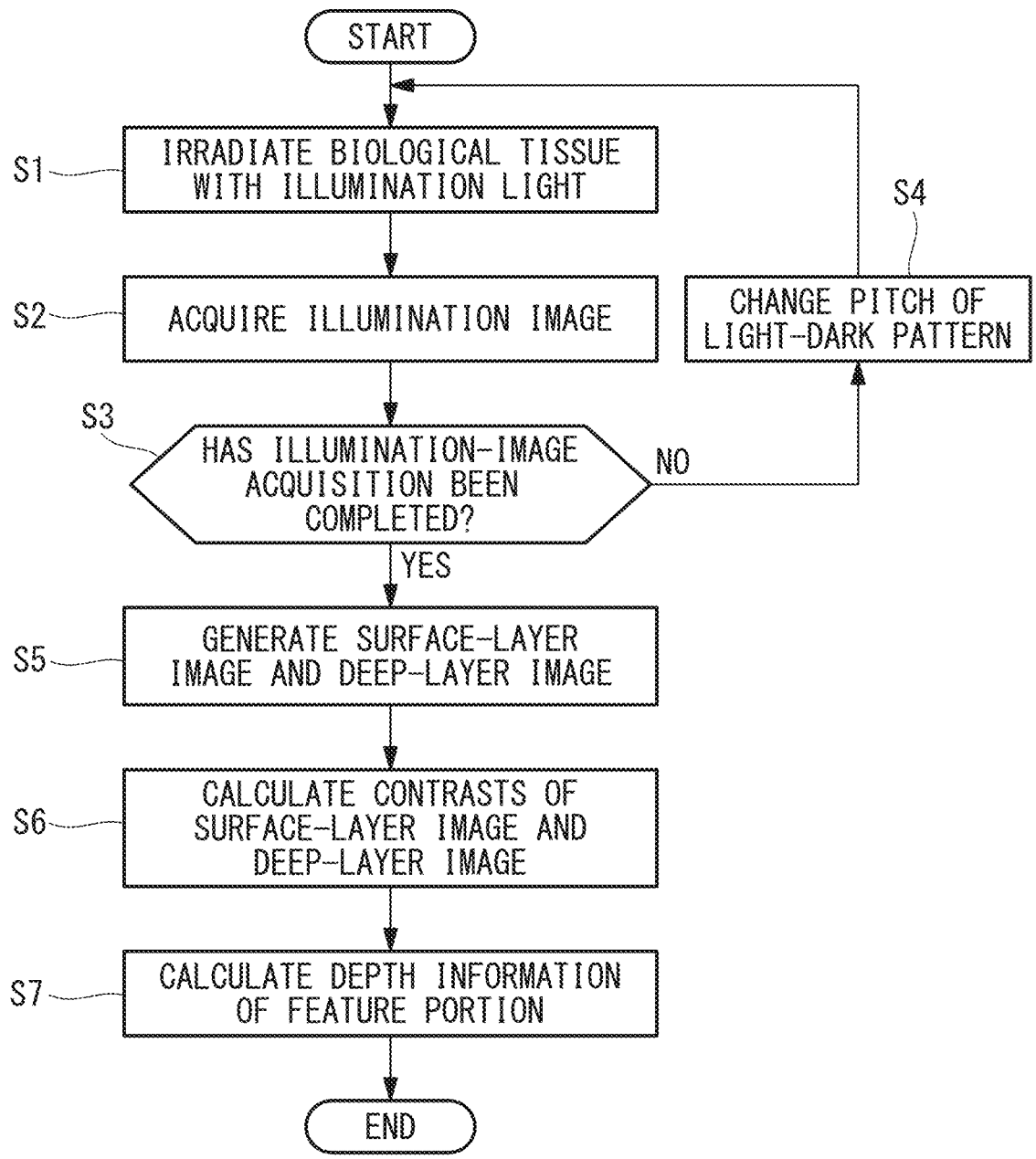
FIG. 9 is a flowchart showing the operation of the endoscope system in FIG. 1.

Next, the operation of the thus-configured endoscope system 1 will be described with reference to FIG. 9.

In order to acquire depth information of a feature portion E in the biological tissue A by using the endoscope system 1 according to this embodiment, the endoscope 2 is inserted into a body and the illumination image of the biological tissue A is acquired. Specifically, the illumination light beam L is radiated onto the biological tissue A from the illumination portion 4 (step S1). The positions of the light portions and the dark portions of the illumination light beam L are changed over time by the intensity-distribution changing portion 5. The image acquisition portion 6 acquires one set of the first illumination image and the second illumination image by executing image capturing at two times at which the light portions and the dark portions are switched with each other (step S2). Next, the pitch P of the illumination light beam L is changed by the intensity-distribution changing portion 5 (step S4), and another set of the first illumination image and the second illumination image are acquired by the image acquisition portion 6 (step S2). Steps S4, S1, and S2 are repeated until the first illumination images and the second illumination images based on the illumination light beam L at all of the pitches P set in advance are acquired ("YES" in step S3).

Next, the separation processing portion 7 generates, from the multiple sets of the first illumination images and the second illumination images, multiple sets of the surface-layer images and the deep-layer images in which the separation depths are different from each other (step S5). Next, the computation portion 8 calculates the contrasts of the respective surface-layer images and those of the respective deep-layer images (step S6). Next, the computation portion 8 calculates the depth information of the feature portion E in the biological tissue A on the basis of changes in the contrasts of the surface-layer images with respect to the separation depths and the changes in the contrasts of the deep-layer images with respect to the separation depths.

As has been described above, with this embodiment, multiple sets of the first illumination images and the second illumination images are acquired by using the illumination light beams L in which the widths Wd of the dark portions are different from each other, and multiple sets of the surface-layer images and the deep-layer images in which the separation depths are different from each other are generated from the multiple sets of the first illumination images and the second illumination images. Also, there is an advantage in that it is possible to calculate the depth information of the feature portion E in the biological tissue A on the basis of the contrasts of the plurality of surface-layer images and the contrasts of the plurality of deep-layer images. In addition, the first and second illumination images are images based on the scattered light beams generated via the biological tissue A and the feature portion E. Therefore, there is an advantage in that it is possible to acquire the depth information of the feature portion E from the first and second illumination images regardless of the absorption characteristics of the feature portion E.

In order to ensure a good balance between the quantity of information about the deep layer D in the surface-layer images and the quantity of information about the deep layer D in the deep-layer images, it is preferable that the widths Wd of the dark portions on the surface B of the biological tissue A be 0.005-25 mm.

In the case in which the widths Wd of the dark portions are less than 0.005 mm, the proportion of the interior scattered light beams that are bent to reach the projection regions of the dark portions from the projection regions of the light portions increases, and, as a result, differences between the intensity values Imax and the intensity values Imin decrease, and thus, the quantity of the surface-layer-C information contained in the surface-layer images could become insufficient. On the other hand, in the case in which widths Wd of the dark portions are greater than 25 mm, the interior scattered light beams cannot reach the centers of the projection regions of the dark portions, and, as a result, the intensity values Imin approach zero, and thus, the quantity of the deep-layer-D information contained in the deep-layer images could become insufficient.

In this embodiment, the illumination portion 4 illuminates the biological tissue A with the illumination light beam L having a stripe-like intensity distribution; however, the intensity distribution pattern of the illumination light beam L is not limited thereto, and other distributions in which the light portions and the dark portions are spatially repeated may be employed. For example, the intensity distribution of the illumination light beam L may be a checkered pattern, dots, or random dots.

Figure 10A:
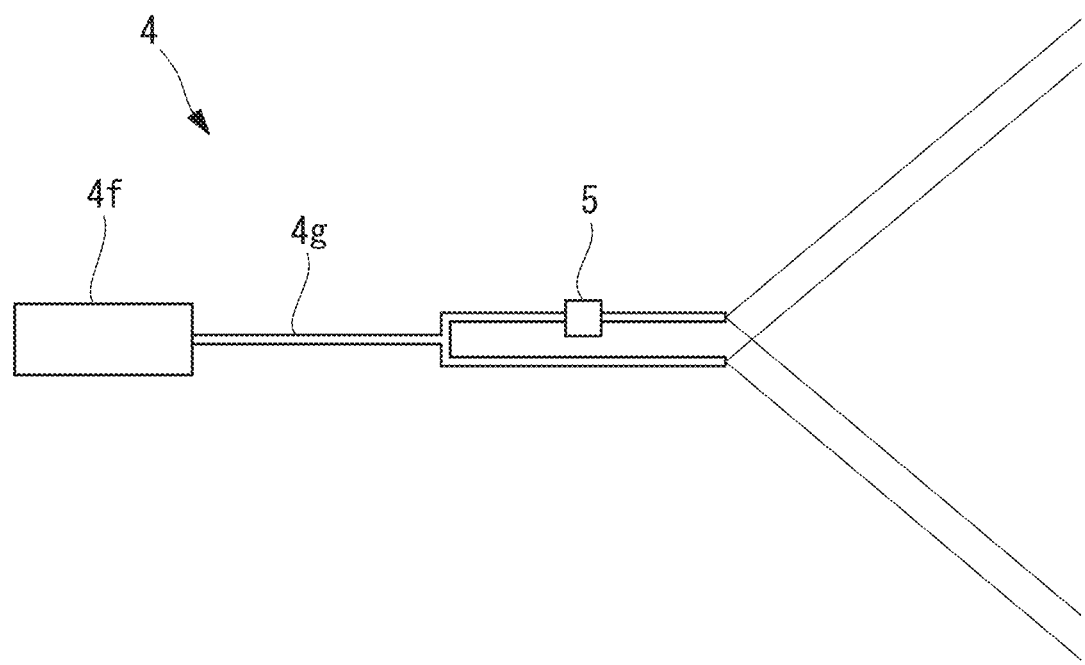
FIG. 10A is a diagram showing another configuration example of an illumination portion and an intensity-distribution changing portion.
Figure 10B:
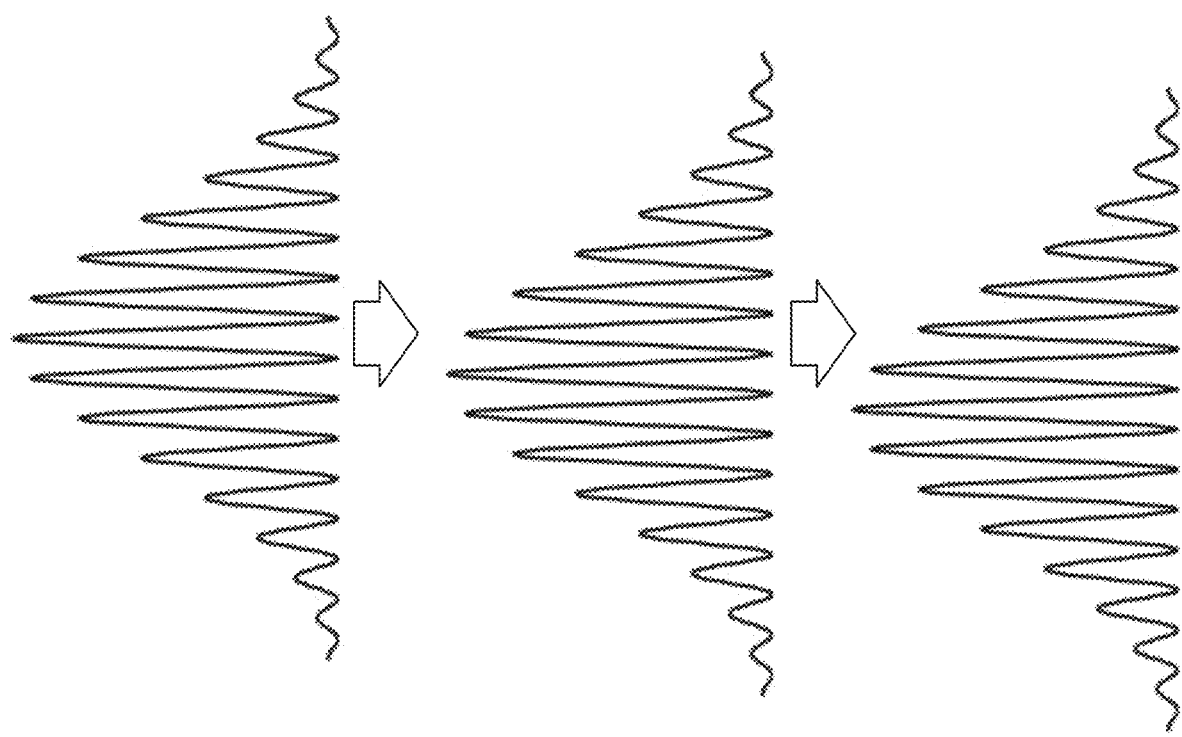
FIG. 10B is a diagram for explaining the light-dark pattern of the illumination light beam generated by the illumination portion in FIG. 10A and the change over time thereof.
Figure 10C:
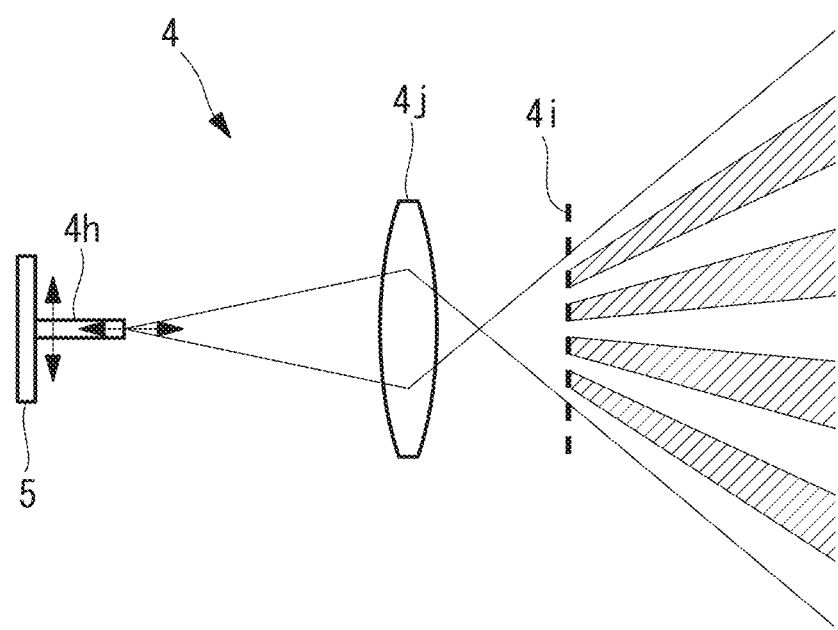
FIG. 10C is a diagram showing another configuration example of the illumination portion and the intensity-distribution changing portion.

In this embodiment, the illumination portion 4 generates the illumination light beam L having a light-dark pattern by means of the liquid crystal element 4c, and the intensity-distribution changing portion 5 causes the light-dark pattern to change by controlling the liquid crystal element 4c; however, the configurations of the illumination portion 4 and the intensity-distribution changing portion 5 are not limited thereto. FIGS. 10A to 10C show examples of other configurations of the illumination portion 4 and the intensity-distribution changing portion 5.

The illumination portion 4 in FIG. 10A utilizes light interference fringes as the light-dark pattern. The illumination portion 4 includes a laser light source 4f and optical paths 4g that split the light output from the laser light source 4f and that emit two light beams. The optical paths 4g are formed from, for example, optical fibers. As a result of the two light beams emitted from the optical paths 4g interfering with each other, interference fringes having a sine-wave-like intensity profile shown in FIG. 10B are generated as the light-dark pattern.

The intensity-distribution changing portion 5 in FIG. 10A causes the position of the interference fringes to shift in a direction orthogonal to the optical axis of the illumination light, as shown in FIG. 10B, by changing the optical-path length of one of the two split light beams. Therefore, the intensity-distribution changing portion 5 includes an optical element that is provided in the optical path of one of the two light beams and that causes the optical-path length to change. In addition, the intensity-distribution changing portion 5 causes the pitch of the interference fringes to change by changing the wavelength of the laser light beam, and, by doing so, the widths Wd of the dark portions are changed. Therefore, the laser light source 4f is, for example, a tunable-wavelength laser light source, and the intensity-distribution changing portion 5 includes a control element that controls the output wavelength of the laser light source 4f.

The illumination portion 4 in FIG. 10C forms the light-dark pattern on the surface B of the biological tissue A in a shadow-picture-like manner. The illumination portion 4 includes a light emitting portion 4h and a mask 4i provided in a distal-end portion of the endoscope 2.

The light emitting portion 4h is, for example, a light source such as a xenon lamp, an LED (RGB), a white LED, or an infrared light source. The light emitting portion 4h may be an emitting end of an optical fiber that is connected to a light source disposed outside the main body portion 3.

The mask 4i has light transmitting regions that allow white light to pass therethrough and light blocking regions that block the white light, and a projection pattern corresponding to the light-dark pattern is formed from the light transmitting regions and the light blocking regions. The mask 4i is, for example, a light blocking substrate on which openings that serve as the light transmitting regions are formed or a transparent substrate on which a light blocking film that serves as the light blocking regions is formed. The illumination light beam L having the light-dark pattern is generated as a result of the light output from the light emitting portion 4h passing through the mask 4i.

A lens 4j that adjusts the divergence angle of the illumination light beam L to be radiated onto the biological tissue A is disposed between the light emitting portion 4h and the mask 4i.

The intensity-distribution changing portion 5 in FIG. 10C causes the intensity distribution to change over time by causing the light emitting portion 4h and the mask 4i to relatively move in the width directions of the light portions and the dark portions. Therefore, the intensity-distribution changing portion 5 includes an actuator that causes at least one of the light emitting portion 4h and the mask 4i to move. In addition, the intensity-distribution changing portion 5 causes the pitches P of the light-dark pattern and the widths Wd of the dark portions to change by changing a spacing between the light emitting portion 4h and the mask 4i in the optical-axis direction. Therefore, the intensity-distribution changing portion 5 includes an actuator that causes at least one of the light emitting portion 4h and the mask 4i to move. With an increase in the spacing between the light emitting portion 4h and the mask 4i, the pitches P of the light-dark pattern on the surface B of the biological tissue A decrease.

In this embodiment, the intensity-distribution changing portion 5 may continuously change the intensity distributions of the illumination light beam L between two light-dark patterns in which the light portions and the dark portions are inverted with respect to each other.

Figure 11A:
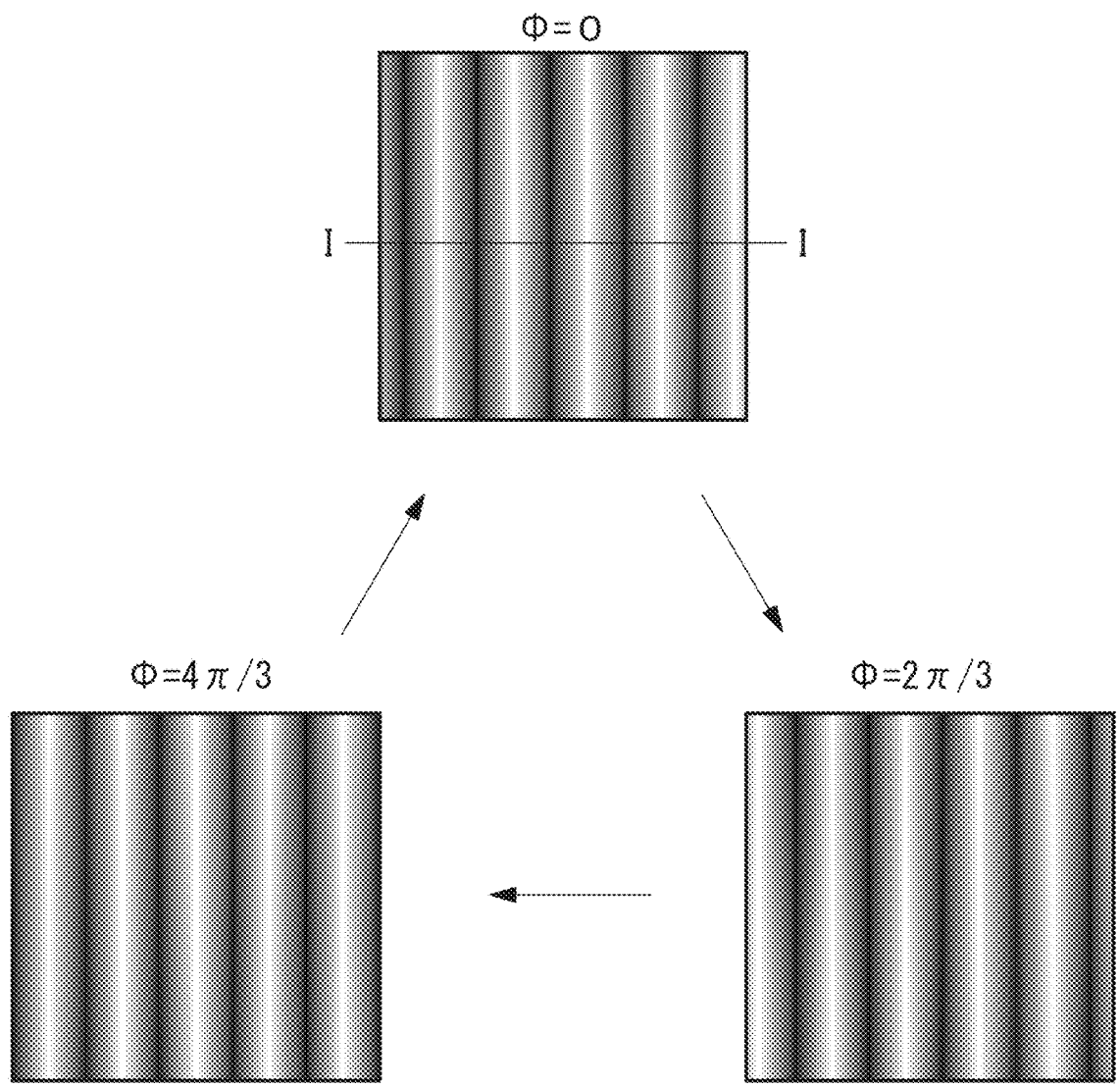
FIG. 11A is a diagram for explaining another example of the change over time in an intensity distribution of the illumination light beam.

In the case in which the light-dark patterns are continuously changed, as shown in FIG. 11A, the image acquisition portion 6 may acquire three or more illumination images in which the positions of the projection regions of the light portions and the projection regions of the dark portions are different from each other by executing image capturing at three or more times at which the positions of the light portions and the dark portions are different from each other. The separation processing portion 7 may create a surface-layer image and a deep-layer image from the three or more illumination images. In this case, because three or more intensity values are obtained for pixels at the respective positions, intensity values Is and Id can be calculated by employing a maximum intensity value as Imax and a minimum intensity value as Imin.

Figure 11B:
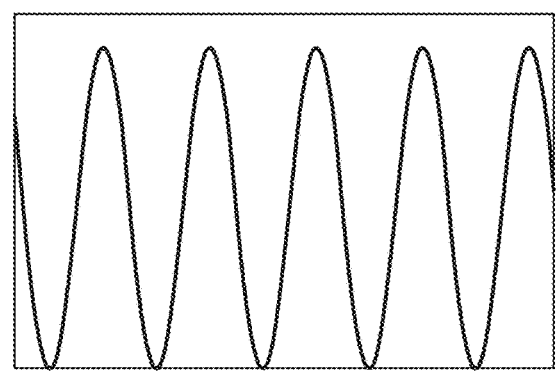
FIG. 11B is a diagram showing a spatial profile of the intensity of the illumination light beam taken along the line I-I in FIG. 11A.

As shown in FIG. 11B, in the case in which the illumination light beam L having a sine-wave-like light-dark pattern is radiated, it is possible to calculate Imax and Imin for each of the pixels by employing a phase shift method by capturing the illumination images under three or more appropriate conditions.

In this embodiment, it is preferable that the illumination portion 4 emit the illumination light beam L, which is a divergent beam, toward the biological tissue A so that the light-dark pattern projected on the surface B of the biological tissue A expands in a proportional manner with respect to the image-capturing distance between the biological tissue A and the image acquisition portion 6.

With this configuration, it is possible to change the widths Wd of the dark portions by expanding or contracting the light-dark pattern on the surface B of the biological tissue A simply by moving the endoscope 2 in a longitudinal direction with respect to the biological tissue A.

This embodiment may additionally include an image-capturing-distance measuring portion that measures an image-capturing distance between the biological tissue A and the image acquisition portion 6, and the intensity-distribution changing portion 5 may adjust the spatial periods of the light portions and the dark portions in the light-dark pattern on the basis of the image-capturing distance so that the spatial periods (pitch P of the light-dark pattern) of the light portions and the dark portions on the surface B of the biological tissue A are kept constant independently of the image-capturing distance.

By employing such a configuration, it is possible to create a deep-layer image containing information about a prescribed depth independently of the image-capturing distance.

As the image-capturing-distance measuring portion, it is possible to employ a publicly known arbitrary means that is capable of measuring the image-capturing distance without coming into contact with the biological tissue A. In the case in which the light-dark pattern is a straight-line stripe pattern in which the intensity changes in a sine-wave-like manner, as shown in FIG. 11B, the image-capturing-distance measuring portion can calculate, by employing a phase shift method, the image-capturing distance from the illumination images acquired by the image acquisition portion 6.

In this embodiment, the illumination portion 4 may illuminate the biological tissue A with an illumination light beam L consisting of a plurality of light beams having wavelengths that are different from each other. For example, the illumination light beam L may be a white light beam in which three light beams, that is, red, green, and blue, are mixed.

In the case in which a plurality of light beams having wavelengths that are different from each other are used as the illumination light beam L, the intensity distributions of the respective light beams may be made to differ in accordance with the wavelengths so that the periods of the light portions and the dark portions are decreased with an increase in the wavelengths.

In general, light is scattered by a scatterer more strongly as the wavelength decreases. Therefore, it is difficult for a blue light beam to reach the deep layer D of the biological tissue A as compared with a red light beam, and information contained in an interior scattered light beam of a blue light beam becomes information about a shallow position as compared with information about an interior scattered light beam of a red light beam. Therefore, by decreasing the periods of the light portions and the dark portions with an increase in the wavelength, it is possible to control the depths of information contained in the interior scattered light beams of the respective colors so that interior scattered light beams of all of the red, green, and blue light beams have information about the same depth.

Figure 12:
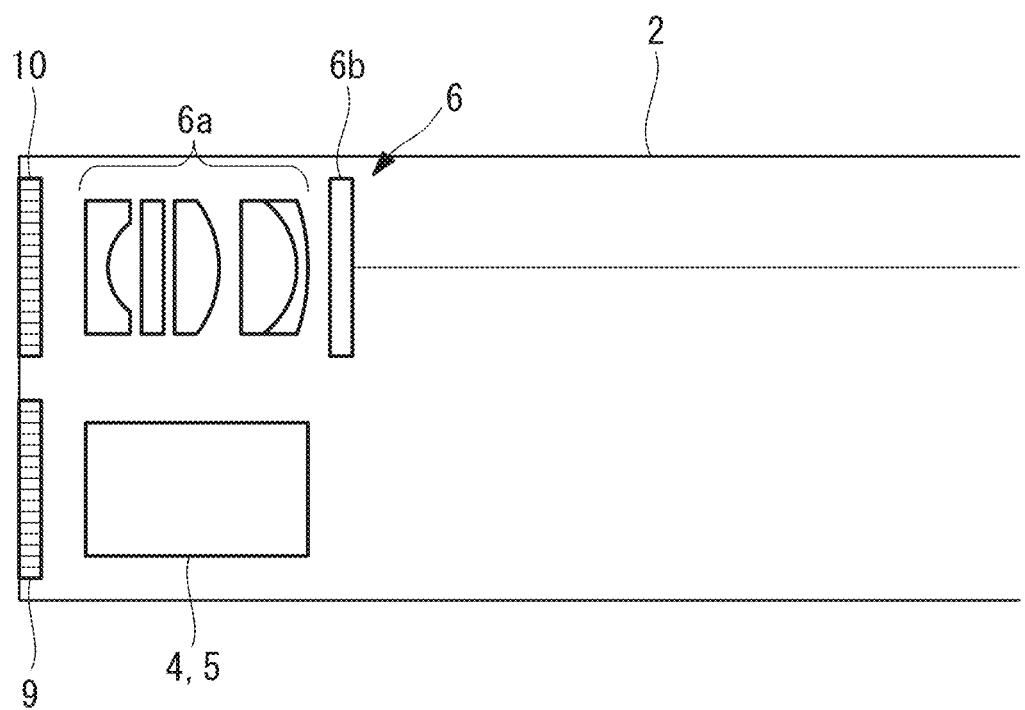
FIG. 12 is a partial configuration diagram of a modification of the endoscope system including a polarization control portion and a polarization selection portion.

In this embodiment, as shown in FIG. 12, a polarizer (polarization control portion) 9 that controls the polarization state of the illumination light beam L emitted from the illumination portion 4 and a polarizer (polarization selection portion) 10 that selects the polarization state of the light that enters the image acquisition portion 6 from the biological tissue A may additionally be provided. The polarizer 9 and the polarizer 10 are provided, for example, at the distal end of the endoscope 2.

The specular light beams are generated in the surface B of the biological tissue A due to the irradiation with the illumination light beam L. The specular light beams contained in the first and second illumination images are separated into the surface-layer images. Therefore, the specular light beams influence the contrasts of the surface-layer images.

The specular light beams have the same polarization states as the illumination light beam L, and the surface scattered light beams and the interior scattered light beams do not have a specific polarization state. Therefore, as a result of setting the polarization direction of the polarizer 9 so as to be orthogonal to the polarization direction of the polarizer 10, it is possible to acquire the first and second illumination images that contain the surface scattered light beams and the interior scattered light beams and that do not contain the specular light beams. Accordingly, it is possible to calculate the contrasts of the surface-layer images based on the feature portion E without being influenced by the specular light beams, and it is possible to enhance the precision of calculating the depth information of the feature portion E.

The above-described embodiment also leads to the following aspects.

An aspect of the present invention is an endoscope system including: an illumination portion that radiates illumination light beam onto an imaging subject, the illumination light beam having intensity distribution in which light portions and dark portions are spatially repeated in a beam cross section perpendicular to an optical axis; an intensity-distribution changing portion that causes widths of the dark portions in the intensity distribution of the illumination light beam to change; an image acquisition portion that acquires a plurality of illumination images of the imaging subject being illuminated with illumination light beams in which the widths of the dark portions are different from each other; a separation processing portion that creates first separation images and second separation images from each of the plurality of illumination images, the first separation images containing a greater quantity of information about a deep layer of the imaging subject than the second separation images do; and a computation portion that calculates information about depths of a feature portion in the imaging subject on the basis of the plurality of the first separation images and the plurality of the second separation images created from the plurality of illumination images, wherein the separation processing portion creates the first and second separation images on the basis of at least two types of intensity values among the intensity values of pixels that are in the illumination images and that respectively correspond to, in the intensity distribution, the light portions, the dark portions, and portions having intensity values that are between those of the light portions and those of the dark portions, and the computation portion calculates the information about the depths of the feature portion on the basis of changes among the plurality of first separation images and changes among the plurality of second separation images.

With this aspect, when the illumination light beams are radiated onto the imaging subject, which is a scatterer, specular reflected light beams (specular light beams), which are generated by specular reflection at the surface of the imaging subject, surface scattered light beams, which are emitted from the surface of the imaging subject after being scattered in the surface layer of the interior of the imaging subject, and interior scattered light beams, which are emitted from the surface of the imaging subject after being scattered in the deep layer in the interior of the imaging subject, are generated. As a result of radiating the illumination light beams, which have spatially nonuniform intensity distributions, onto the imaging subject from the illumination portion, the interior scattered light beams are spatially separated from the specular light beams and the surface scattered light beams. In other words, the specular light beams, the surface scattered light beams, and the interior scattered light beams are generated in the light portions, whereas the interior scattered light beams, which have been bent to reach the dark portion from the light portion, are predominantly generated in the dark portions.

Therefore, regions corresponding to the dark portions in the illumination images acquired by the image acquisition portion contain a large quantity of information about the deep layer, and the regions corresponding to the light portions contain a large quantity of information about the surface and the surface layer. The information refers to, for example, the light level of light that enters the biological tissue and that is emitted from the biological tissue after being subjected to modulation such as scattering or absorption due to the biological tissue and a structure in the interior thereof. The separation processing portion can create the first and second separation images, which contain a large quantity of information about different depths, on the basis of at least two types of intensity values among the intensity values of pixels that respectively correspond to the light portions, the dark portions, and the portions having intensity values that are between those of the light portions and those of the dark portions.

Specifically, the separation processing portion can create the first separation images (deep-layer images), which contain a large quantity of information about the deep layer of the imaging subject, on the basis of the intensity values of the pixels of the regions corresponding to the dark portions.

In addition, the separation processing portion can create the second separation images (surface-layer images), which contain a large quantity of information about the surface and the surface layer of the imaging subject, on the basis of the intensity values of the pixels of the regions corresponding to the light portions. Alternatively, the separation processing portion can create the second separation images, which contain a large quantity of information about a position that is shallower than the deep layer and that is deeper than the surface layer, on the basis of the intensity values of the pixels of the regions corresponding to the portions having intensity values that are between those of the light portions and those of the dark portions.

In this case, the widths of the dark portions of the illumination light beams to be radiated onto the imaging subject are changed by the intensity-distribution changing portion, and the image acquisition portion acquires a plurality of illumination images of the imaging subject being illuminated by the illumination light beams in which the widths of the dark portions are different from each other. Separation depths between the first and second separation images increase with an increase in the widths of the dark portions in the imaging subject. A separation depth is an approximate boundary between depths of the information contained in the first and second separation images. In other words, the first separation images mainly contain information about deeper layers than the separation depths, and the second separation images mainly contain information about shallower layers than the separation depths. The first separation images contain the information about shallower layers with a decrease in the widths of the dark portions, and the second separation images contain the information about deeper layers with an increase in the widths of the dark portions. Therefore, it is possible to acquire depth information of a feature portion in the imaging subject on the basis of the changes in the plurality of first separation images and the plurality of the second separation images created from the plurality of illumination images. In addition, as a result of using the illumination images based on the scattered light beams generated due to the feature portion, it is possible to acquire the depth information of the feature portion regardless of the absorption characteristics of the feature portion.

In the above-described aspect, the illumination portion may emit the illumination light beam in a form of divergent beam so that pattern of the light portions and the dark portions on the imaging subject expands in a proportional matter with respect to an image-capturing distance between the image acquisition portion and the imaging subject.

With this configuration, it is possible to change the widths of the dark portions on the imaging subject simply by changing the image-capturing distance.

The above-described aspect may include an image-capturing-distance measuring portion that measures an image-capturing distance between the image acquisition portion and the imaging subject, wherein the intensity-distribution changing portion may change periods of the light portions and the dark portions in the intensity distribution on the basis of the image-capturing distance so that the intensity distribution of the illumination light beam on the imaging subject becomes constant independently of a distance between the image acquisition portion and the imaging subject.

With this configuration, it is possible to set the relationship between the widths of the dark portions in the illumination portion and the widths of the dark portions on the imaging subject to be constant independently of the image-capturing distance.

In the above-described aspect, the illumination light beam may consist of a plurality of light beams having wavelengths that are different from each other, and the plurality of light beams have the intensity distribution in which periods of the light portions and the dark portions decrease with an increase in the wavelengths.

Because the light that has entered the imaging subject reaches a deeper position with an increase in the wavelength thereof, the interior scattered light beams of light having greater wavelengths contain information about deeper layers. It is possible to decrease differences in the depths of the information due to differences in the wavelengths by decreasing the period of the light portions and the dark portions with an increase in the wavelengths.

In the above-described aspect, the intensity distribution of the illumination light beam may have a stripe-like pattern in which the band-like light portions and dark portions are repeated in an alternating manner in a width direction.

With this configuration, it is possible to effectively separate the interior scattered light beams by means of a simple light-dark pattern. In addition, to create the first and second separation images having high resolutions, two or more illumination images of the imaging subject being illuminated with the illumination light beams in which the positions of the light portions and the dark portions are different from each other are used. It is possible to change, over time, the positions of the light portions and the dark portions in a simple manner by changing the intensity distribution only in the width directions of the stripes.

In the above-described aspect, an intensity profile of the light portions and the dark portions of the intensity distribution of the illumination light beam in the width direction may have a substantially sine-wave shape.

As a result of radiating, onto the imaging subject, the illumination light beams in which the intensity spatially changes in a sine-wave-like manner, it is possible to calculate, by means of a phase shift method, the intensity value for the second separation image when the most intense light is being radiated and the intensity value for the first separation image when the least intense light is being radiated. Accordingly, it is possible to create the first and second separation images having high resolutions from a small number of the illumination images.

The above-described aspect may include: a polarization control portion that controls polarization states of the illumination light beam; and a polarization selection portion that selects a polarization state of light coming into the image acquisition portion from the imaging subject.

When the illumination light beams are radiated onto the imaging subject, specular reflected light beams (specular light beams) can also be generated in addition to the surface scattered light beams and the interior scattered light beams. The specular light beams are light generated by specular reflection at a surface of the imaging subject, and is contained in the second separation images. The specular light beams have the same polarization state as the illumination light beams, whereas the surface scattered light beams and the interior scattered light beams do not have a specific polarization state. Therefore, as a result of selectively making light other than the specular light beams enter the image acquisition portion by means of the polarization selection portion, it is possible to create second separation images that do not contain the specular light beams. Also, it is possible to acquire more accurate information about the depths of the feature portion on the basis of the second separation images that do not contain the specular light beams.

In the above-described aspect, the computation portion may calculate the information about the depths of the feature portion on the basis of a correspondence table in which the widths of the dark portions and separation depths between the first separation images and the second separation images are associated with each other.

With this configuration, it is possible to know the depths of layers, the information of which is contained in the individual separation images, from the separation depths associated with the widths of the dark portions in the correspondence table. Therefore, it is possible to calculate the information about the depths of the feature portion in a simple manner by acquiring the separation depths of the separation images containing the feature portion from the correspondence table.

In the above-described aspect, the computation portion may respectively calculate contrasts of multiple sets of the first and second separation images, and calculates the information about the depths of the feature portion on the basis of the contrasts and the correspondence table.

The contrasts of the separation images that contain the feature portion become higher than the contrasts of the separation images that do not contain the feature portion. Therefore, it is possible to easily identify the separation images that contain the feature portion on the basis of the contrasts thereof. Also, it is possible to calculate the information about the depths of the feature portion by acquiring the separation depths associated with the widths of the dark portions of the identified separation images from the correspondence table.

REFERENCE SIGNS LIST

1 endoscope system
2 endoscope
3 main body portion
4 illumination portion
5 intensity-distribution changing portion
6 image acquisition portion
7 separation processing portion
8 computation portion
A biological tissue (imaging subject)
B biological-tissue surface
C surface layer
D deep layer
E feature portion
Wd dark-portion width

The invention claimed is:

1. An endoscope system comprising:
an illumination portion that comprises an emitter and that is configured to radiate illumination light beam onto an imaging subject, the illumination light beam having intensity distribution in which light portions and dark portions are spatially repeated in a beam cross section perpendicular to an optical axis;
a controller configured to cause widths of the dark portions in the intensity distribution of the illumination light beam to change;
an imager configured to acquire a plurality of illumination images of the imaging subject being illuminated with illumination light beams in which the widths of the dark portions are different from each other; and
at least one processor comprising hardware, the processor being configured to:
create first separation images and second separation images from each of the plurality of illumination images, the first separation images containing a greater quantity of information about a deep layer of the imaging subject than the second separation images do; and
calculate information about depths of a feature portion in the imaging subject on the basis of the plurality of the first separation images and the plurality of the second separation images created from the plurality of illumination images,
wherein the processor is configured to:
create the first and second separation images on the basis of at least two types of intensity values among the intensity values of pixels that are in the illumination images and that respectively correspond to, in the intensity distribution, the light portions, the dark portions, and portions having intensity values that are between those of the light portions and those of the dark portions; and
calculate the information about the depths of the feature portion on the basis of changes among the plurality of first separation images and changes among the plurality of second separation images.

2. The endoscope system according to claim 1, wherein the illumination portion is configured to emit the illumination light beam in a form of divergent beam so that pattern of the light portions and the dark portions on the imaging subject expands in a proportional matter with respect to an image-capturing distance between the imager and the imaging subject.

3. The endoscope system according to claim 1, further comprising:
a meter configured to measure an image-capturing distance between the imager and the imaging subject,
wherein the controller is configured to change periods of the light portions and the dark portions in the intensity distribution on the basis of the image-capturing distance so that the intensity distribution of the illumination light beam on the imaging subject becomes constant independently of a distance between the imager and the imaging subject.

4. The endoscope system according to claim 1, wherein the illumination light beam consists of a plurality of light beams having wavelengths that are different from each other, and the plurality of light beams have the intensity distribution in which periods of the light portions and the dark portions decrease with an increase in the wavelengths.

5. The endoscope system according to claim 1, wherein the intensity distribution of the illumination light beam has a stripe-like pattern in which the band-like light portions and dark portions are repeated in an alternating manner in a width direction.

6. The endoscope system according to claim 5, wherein an intensity profile of the light portions and the dark portions of the intensity distribution of the illumination light beam in the width direction has a substantially sine-wave shape.

7. The endoscope system according to claim 1, further comprising:
 a first polarizer configured to control polarization states of the illumination light beam; and
 a second polarizer configured to select a polarization state of light coming into the imager from the imaging subject.

8. The endoscope system according to claim 1, wherein the processor is configured to calculate the information about the depths of the feature portion on the basis of a correspondence table in which the widths of the dark portions and separation depths between the first separation images and the second separation images are associated with each other.

9. The endoscope system according to claim 8, wherein the processor is configured to:
 respectively calculate contrasts of multiple sets of the first and second separation images; and
 calculate the information about the depths of the feature portion on the basis of the contrasts and the correspondence table.

* * * * *